(12) United States Patent
Andreasson

(10) Patent No.: US 11,612,728 B2
(45) Date of Patent: Mar. 28, 2023

(54) DEVICE FOR COSMETIC TREATMENTS

(71) Applicant: CAMPOMATS S.R.L. UNIPERSONALE, Carpi (IT)

(72) Inventor: Mats Andreasson, Landvetter (SE)

(73) Assignee: CAMPOMATS S.R.L. UNIPERSONALE

( * ) Notice: Subject to any disclaimer, the term of this patent is extended or adjusted under 35 U.S.C. 154(b) by 322 days.

(21) Appl. No.: 17/010,981

(22) Filed: Sep. 3, 2020

(65) Prior Publication Data

US 2021/0060324 A1 Mar. 4, 2021

(30) Foreign Application Priority Data

Sep. 4, 2019 (IT) .................. 102019000015560

(51) Int. Cl.
*A61M 37/00* (2006.01)
*A45D 44/00* (2006.01)

(52) U.S. Cl.
CPC .......... *A61M 37/0015* (2013.01); *A45D 44/00* (2013.01); *A61M 2205/8206* (2013.01)

(58) Field of Classification Search
CPC ...... A61M 37/0015; A61M 2205/8206; A61M 37/0076; A61M 37/0084; A45D 44/00
See application file for complete search history.

(56) References Cited

U.S. PATENT DOCUMENTS 3,663,162 A 5/1972 Randhava et al.
9,629,991 B1 4/2017 O'Brien, III et al.
9,636,491 B1 * 5/2017 O'Brien, III ...... A61M 37/0015

FOREIGN PATENT DOCUMENTS

DE 20013579 U1 3/2001

* cited by examiner

*Primary Examiner* — Amber R Stiles
(74) *Attorney, Agent, or Firm* — Laubscher & Laubscher PC

(57) ABSTRACT

A device for cosmetic treatment, in particular for permanent make-up, micro-needling or micro-pricking treatments, including a body having a first section, arranged at a first end of the body, in which a drive motor of the device (1) is arranged, a second section, arranged at a second end of the body, opposite the first end, in which a needle-holding cartridge can be fitted, and a third section, that connects the first section to the second section, in which drive means is housed of the needles contained in said needle-holding cartridge. The needle-holding cartridge includes a support element configured for supporting a single needle, or a plurality of needles and is movable inside a casing. of the cartridge The needle-holding cartridge is driven to move inside the casing by the drive means between a variable start position and a variable end position for a preset distance.

9 Claims, 5 Drawing Sheets

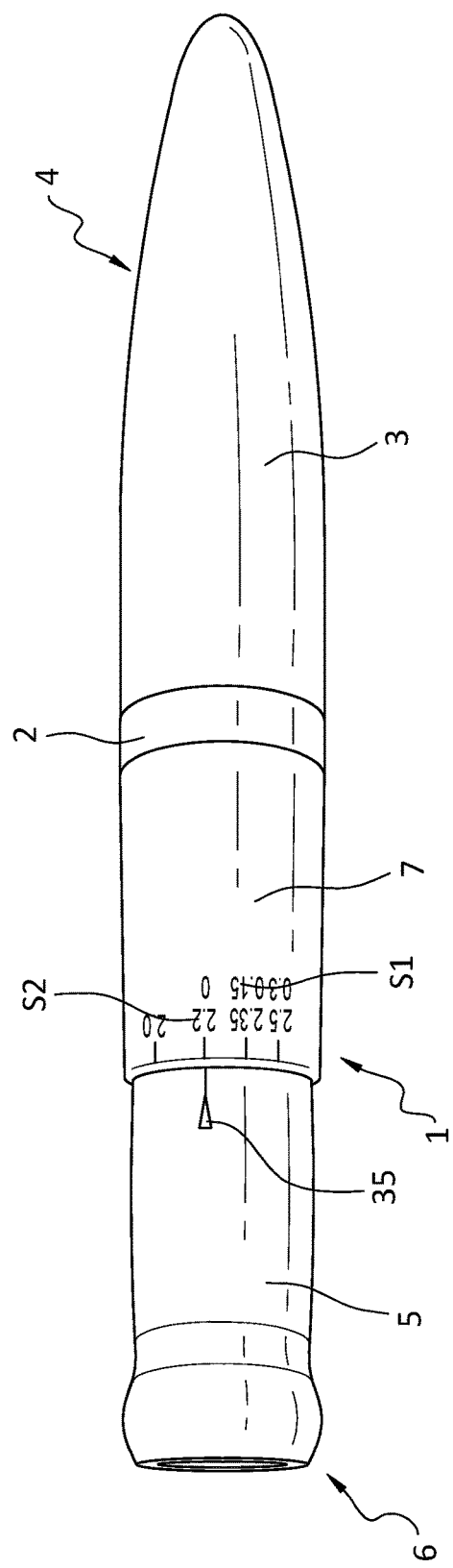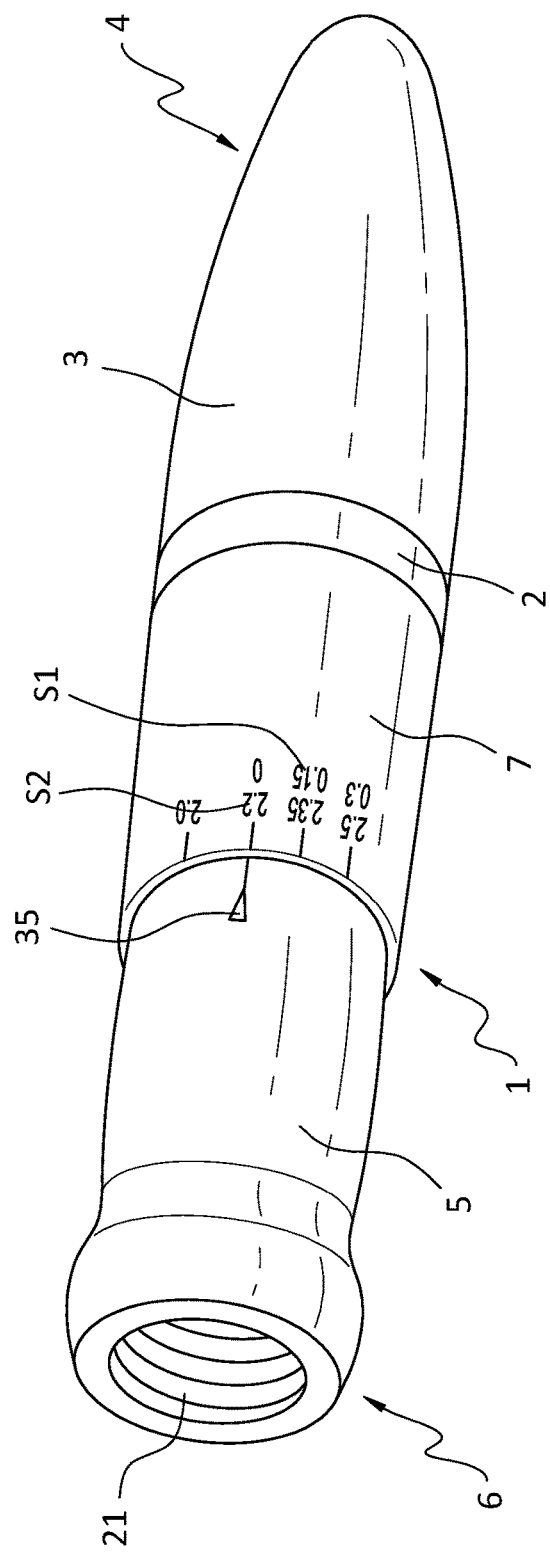

DEVICE FOR COSMETIC TREATMENTS

CROSS-REFERENCE TO RELATED APPLICATIONS

This application claims priority of Italian Patent Application No. 102019000015560 filed on Sep. 4, 2019, entitled "Device for Cosmetic Treatments." The entire content of this application is incorporated herein by reference.

BACKGROUND OF THE INVENTION

The invention relates to a device for cosmetic treatment, in particular a device for so-called PMU (permanent make-up) treatment, i.e. treatment for applying tattoos or semi-permanent make-up, such as for example making tattooed eyebrows, lips and outlines, eyeliner, or tattooed areolas around nipples for women who have undergone a mastectomy, and micro-needling or micro-pricking intended, for example, to smooth wrinkles, to remove scars or to increase the tone of the skin in a treatment zone, stimulating the production of collagen.

BRIEF SUMMARY OF THE INVENTION

Devices are known consisting of a body, that can be grasped by an operator and on which a cartridge-shaped operating element can be fitted comprising a casing, inside which a needle-holding unit is arranged which consists of a support element to which a single needle or a plurality of needles can be fixed.

The needle-holding unit can slide inside the casing of the cartridge so that the ends of the needles can exit the cartridge and the body of the device. Sliding of the needle-holding unit being controlled by a drive device fitted inside the body of the device and driven by an electric motor.

The type of needle to be used depends on the type of treatment to be administered. For example, for applying tattoos or a semipermanent make-up, a cartridge with a single needle or with a group of three or five needles is generally used, whereas for micro-needling or micro-pricking treatments cartridges with a high number of needles are used, also up to several dozen together.

Also the depth of penetration of the needle or of the needles in the skin depends on the treatment to be applied and can vary from a few tenths of a millimetre to some millimetres, for example from 0.15 mm to 2.5 mm.

In devices known from the prior art, the body of the device is normally set up for fitting of a single type of cartridge, it being necessary for an operator to have at his or her disposal different bodies if he or she wishes to apply different types of treatment. However, devices also exist that can fit different types of cartridge, without however having the possibility of measuring with precision the depth of penetration of the needles in the various types of treatment.

In fact, even if it is possible to adjust the depth of penetration of the needle, or of the needles, the adjusting systems available in devices known from the prior art, that can fit all the types of cartridge, with a number of needles that is variable from 1 to 80, for the various treatments do not permit precise adjustment but only rough adjustment of the depth of penetration of the needles, without any use of a millimetric measuring scale.

Further, if it is possible to fit different types of needle to the device, it is not possible to adjust, if not visually, i.e. very imprecisely, the depth of penetration of the needles.

U.S. Pat. No. 9,629,991 B1 discloses a device for cosmetic treatment comprising a body consisting of a first section, arranged at a first end of the body, in which a drive motor of the device is installed, a second section, arranged at a second end of the body, opposite the first end, in which a needle-holding cartridge is inserted, and a third section, that connects the first section to the second section and in which the drive means is housed to drive the needles contained in the needle-holding cartridge, wherein the needle-holding cartridge comprises a support element configured for supporting a plurality of needles, wherein the support element is movable inside a casing of the cartridge and is driven to move inside the housing by the drive means between a start position in which the needles do not protrude outside the body and an end position in which the needles protrude outside the body for a preset distance, wherein the third section comprises an adjusting ring nut that can rotate around a longitudinal axis of the body, wherein a rotation of the ring nut determines a variation of the start position of the support element and of the preset distance.

U.S. Pat. No. 8,663,162 B2 discloses a device for injecting a fluid into the skin of a subject, for example for removing a tattoo. The fluid is injected by a needle fitted in a cartridge that is inserted into the body of the device. The depth of penetration of the needle can be adjusted. On the body of the device there is a graduated scale that indicates the depth of penetration of the needle.

DE 20013579 U1 discloses a device for dosing insulin to be injected into a diabetic patient. The device comprises adjusting means provided with graduated scales for setting the quantity of insulin to be injected. The device does not comprise any means for adjusting the depth of penetration of the needle by means of which the insulin is injected.

One object of the present invention is to provide a device for cosmetic treatment, as PMU treatments, micro-needling or micro-prickling treatments, and other treatments known as nano treatments, that can use a plurality of types of needle-holding cartridge. The term "nano treatments" means treatments with a depth of penetration of the needles that is not greater than 0.15 mm.

Another object of the present invention is to provide a device for cosmetic treatment, that, in addition to be able to use a plurality of types of needle-holding cartridges enables the depth of penetration of the needles to be adjusted with great precision, for each type of treatment.

A further object of the present invention is to provide a device for cosmetic treatment that is cheap to manufacture and is easy to use.

The objects of the invention are achieved with a device for cosmetic treatment according to claim 1.

Owing to the invention, it is possible to use in a same device a plurality of needle-holding cartridges of different type, without having to modify the part of the device into which the needle-holding cartridge is inserted.

It is further possible to adjust with precision the protrusion of the needles, i.e. the depth of penetration of the needles into the skin of a patient, for any type of cartridge used.

BRIEF DESCRIPTION OF THE DRAWINGS

Further features and advantages of the invention are shown in the description that follows, with reference to the attached drawings, in which:

FIG. 1 is a side view of a device for cosmetic treatment according to the invention;

FIG. 2 is a perspective view of the device of FIG. 1;

DETAILED DESCRIPTION

Figure 3:
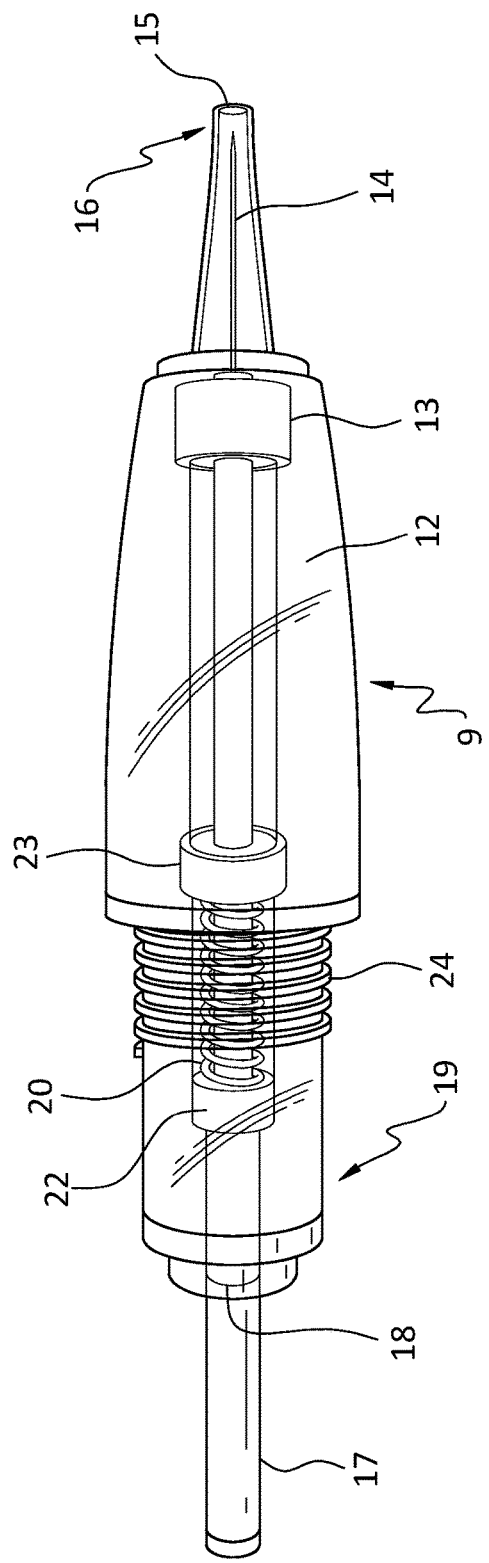
FIG. 3 is a side view of a needle-holding cartridge that can be fitted in the device according to the invention to perform permanent make-up treatments, i.e. treatment for applying tattoos or semipermanent make-up.
Figure 4:
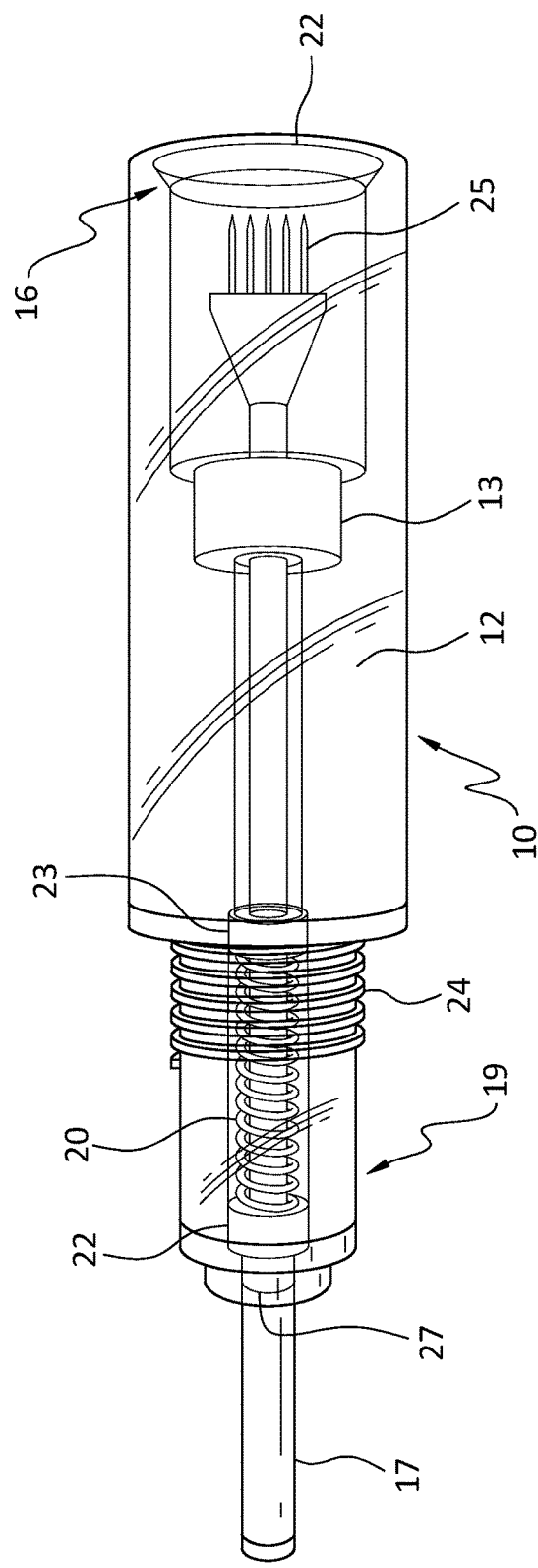
FIG. 4 is a side view of a needle-holding cartridge that can be fitted in the device according to the invention to perform micro-needling or micro-pricking treatments.
Figure 5:
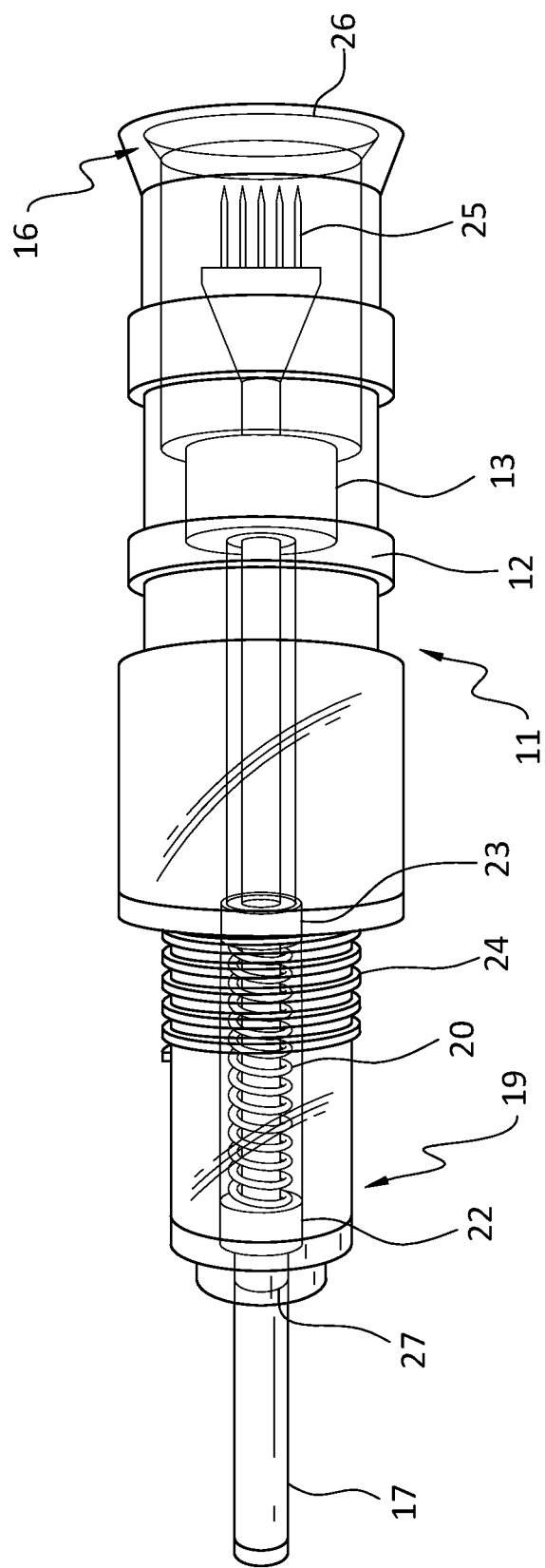
FIG. 5 is a side view of another needle-holding cartridge that can be fitted in the device according to the invention to perform micro-needling or micro-pricking treatments.
Figure 6:
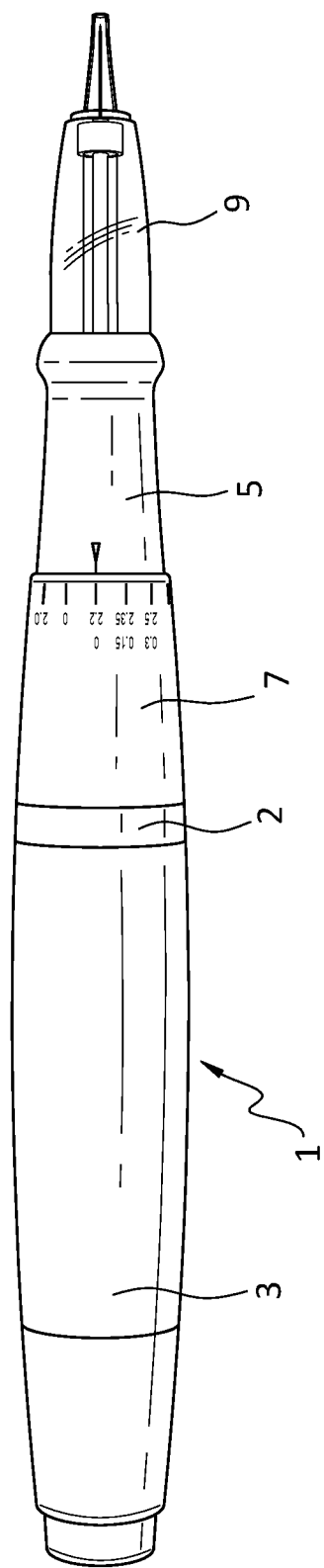
FIG. 6 is a view of the device according to the invention, on which a needle-holding cartridge has been fitted of the type illustrated in FIG. 3.

In FIGS. 1 and 2, a device 1 according to the invention is illustrated that comprises a body 2 divided into three sections: a first section 3, arranged at a first end 4 of the body 2, in which a drive motor is installed (not shown) of the device 1; a second section 5 arranged at a second end 6 of the body 2, opposite the first end 4, in which one of the needle-holding cartridges can be fitted that are illustrated in FIGS. 3, 4 and 5; a third section 7, that connects the first section 3 to the second section 5, in which drive means of the needles that are contained in said needle-holding cartridges are housed.

In FIGS. 3, 4 and 5, three different needle-holding cartridges are shown, respectively a first needle-holding cartridge 9, which is used to perform permanent make-up treatments, a second needle-holding cartridge 10, which is used to perform micro-needling treatments or micro pricking (i.e. a needling treatment with maximum exit of the needles of 0.3 mm) and a third needle-holding cartridge 11, which is also used to perform micro-needling treatments, with exit of the needles, up to 2.5 mm.

The parties of the needle-holding cartridges having the same function are indicated by the same reference numbers.

The first needle-holding cartridge 9 comprises a casing 12, which can be transparent or semitransparent, inside which a support element 13 is arranged, which can slide axially inside the casing 12. To the support element 13 a single needle 14 is fixed that can protrude from the casing 12 through a hole 15 placed at a first end 16 of the casing 12. The support element 13 is made in such a manner that the maximum protrusion of the single needle 14 from the hole 15 is 2.5 mm.

The support element 13 is provided with a rod-shaped appendage 17, which protrudes from the casing 12 through an opening 18 arranged at a second end 19 of the casing 12, opposite the first end 16.

On the rod-shaped appendage 17 a coil spring 20 is fitted, arranged between a first collar 22 that is part of the appendage 17 and a second collar 23 obtained in the casing 12.

The casing 12 is provided with an outer thread 24 by which the first needle-holding cartridge 9 can be tightened in a threaded hole 21 (FIG. 2) made at the second end 6 of the body 2 of the device 1 according to the invention.

The second needle-holding cartridge 10 also comprises a casing 12, which can be transparent or semitransparent, inside which a support element 13 is arranged, which can slide axially inside the casing 12. To the support element 13 a plurality of needles 25 is fixed that can protrude from the casing 12 through a first opening 26 arranged at a first end 16 of the second casing 12.

The support element 13 is so made that the maximum protrusion of each needle of said plurality of needles 25 from said first opening 26 is 0.3 mm.

The support element 13 is provided with a rod-shaped appendage 17, which protrudes from the casing 12 through a second opening 27 arranged at a second end 19 of the second casing 12, opposite the first end 16.

On the rod-shaped appendage 17 a coil spring 20 is fitted, arranged between a first collar 22 that is part of the appendage 17 and a second collar 23 obtained in the casing 12.

The casing 12 is provided with an outer thread 24 by which the second needle-holding cartridge 10 can be tightened in said threaded hole 21.

The third needle-holding cartridge 11 also comprises a casing 12, which can be transparent or semitransparent, inside which a support element 13 is arranged, which can slide axially inside the casing 12. On the support element 13 a plurality of needles 25 is fixed that can protrude from the casing 12 through a first opening 26 arranged at a first end 16 of the second casing 12.

The support element 13 is so made that the maximum protrusion of each needle of said plurality of needles 25 from said first opening 26 is 2.5 mm.

The support element 13 is provided with a rod-shaped appendage 17, which protrudes from the casing 12 through a second opening 27 arranged at a second end 19 of the casing 12, opposite the first end 16.

On the rod-shaped appendage 17 a coil spring 20 is fitted, arranged between a first collar 22 that is part of the appendage 17 and a second collar 23 obtained in the casing 12.

The casing 12 is provided with an outer thread 24 by which the third needle-holding cartridge 10 can be tightened in said threaded hole 21.

The first cartridge 9, the second cartridge 10 and the third cartridge 11, in addition to possible other types of cartridges with other types of needles, are suitable for being fitted in the same threaded hole 21, so that it is not necessary to change the second section 5 of the body 2 if the type of cartridge used changes. This gives the device 1 according to the invention great versatility, with minimized costs, because a single body 2 is required for all types of usable cartridge.

Figure 7:
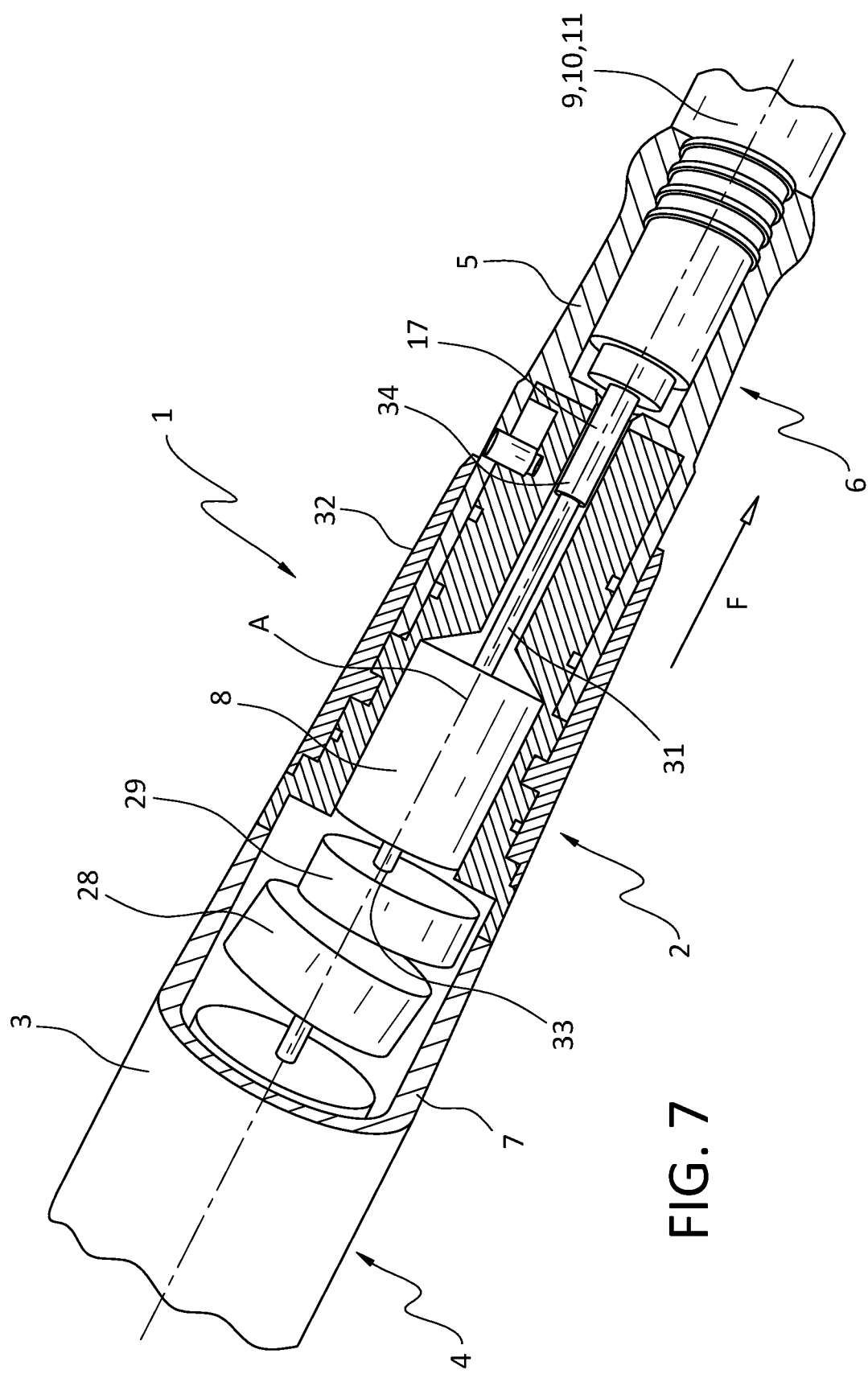
FIG. 7 is a partial perspective view of the device according to the invention, partially sectioned with a plane passing through a longitudinal axis of the device.

In FIG. 7 a perspective partially sectioned partial view is shown of the device 1 according to the invention.

In the third section 7 of the body 2 drive means 28, 29, 30 and 31 are arranged, by means of which the support element 13 is driven to move with reciprocal motion, at a set frequency, along a longitudinal axis A of the body 2.

Through the motion of the support element 13, the needle 14, or the plurality of needles 25, are made to emerge, at said set frequency, from the first end 16 of the casing 12 from the respective needle-holding cartridge 9, 10, 11.

The drive means 28, 29, 30 and 31 comprises a first thrust element 28 fitted to an outlet shaft (that is not visible in FIG. 7) of the drive motor of the device 1.

The first thrust element has the shape of a disc 28 fitted to said outlet shaft that is tilted with respect to said longitudinal axis A. By driving the drive motor, the disc 28 interacts periodically, at said set frequency, with a further disc 29 fitted eccentrically to a first end 33 of a rod-shaped second thrust element 31, arranged along the longitudinal axis A of the body 2. The second thrust element 31 is guided inside a guide element 8 arranged in said third section 7 of the body 2.

A second end 34 of said second thrust element 31 is in contact with the appendage 17 of the support element 13 of the needle-holding cartridge 9, 10, 11, when the cartridge is screwed into the threaded hole 21.

During rotation thereof, the first thrust element 28 comes into contact with the further disc 29 and push the further disc 29 to the second end 6 of the body 2, in the direction of the arrow F, together with the second thrust element 31 which, in turn, pushes the appendage 17 of the support element 13 in the direction of the arrow F, making the needle 14, or the plurality of needles 25 emerge from the first end of the body 2.

During a first half of a complete revolution around the longitudinal axis A, the first thrust element 28 exerts on the further disc 29 a progressively increasing thrust from a minimum value to a maximum value. This thrust is transmitted to the second thrust element 31 and, from the second thrust element 31, to the appendage 17 of the support element 13, so that the latter moves, from a set start position, in the direction of the arrow F, compressing the coil spring 20, to make the needle 14, or the plurality of needles 25 emerge progressively from the first end 6 of the body 2, until it reaches an end position in which the needles reach a preset maximum protrusion from the end 6 of the body 2.

During a second half of said complete revolution, the thrust exerted by the first thrust element 28 on the further disc 29 decreases progressively from said maximum value to said minimum value, determining progressive release of the coil spring 20, which causes a shift of the support element 13, of the appendage 17 thereof, of the second thrust element 31 and of the further disc 29 a direction opposite that of the arrow F, until the support element 13 is returned to said preset start position.

The third section 7 of the body 2 comprises an adjusting ring nut 32 that can rotate around said longitudinal axis A.

By rotating the ring nut 32, the maximum protrusion of the needle 14, or the plurality of needles 25 from the first end 6 of the body 2 can be adjusted, by varying the preset start position of the support element 13.

A rotation of the ring nut 32 determines a shift of the second section 5 of the body 2 with respect to the third section 7, which causes a shift of the support element 13 inside the casing 12 of the cartridge 9, 10, 11, through the effect of the interaction between the appendage 17 of the support 13 and the second thrust element 31, which determines a variation of the initial compression of the coil spring 20. Initial compression of the coil spring 20 means the compression that is exerted on the spring when the value of the thrust exerted by the thrust element 28 on the further disc 29 is minimal.

On the outer surface of the ring nut 32, a first graduated scale S1 and a second graduated scale S2 are impressed. On the second section 5 of the body 2 an indicating element 35 is impressed that is associated with both the graduated scales.

The first graduated scale S1 shows values varying from 0 to 0.3, whereas the second scale S2 shows values varying from 0 to 2.5. The aforesaid values of the first scale S1 and of the second scale S2 indicate the protrusion in millimetres of the needle 14 or of the plurality of needles 25 from the first end 6 of the body 2, when the support element 13 is in said end position.

The scale S1 is used when a needle-holding cartridge is fitted to the body 2 like, for example, the second cartridge 10, configured in such a manner that the maximum protrusion of the needles 25 is 0.3 mm.

This type of cartridge is used for example for wrinkle-smoothing treatments or soft rejuvenation of skin in a less invasive manner than traditional needling treatment.

The scale S2 is used when a needle-holding cartridge is fitted to the body 2 like, for example, the first cartridge 9 or the third cartridge 11, so configured that the maximum protrusion of the needles 14, 25 is 2.5 mm.

This type of cartridge can be used for traditional microneedling treatments, for removing scars, or for permanent make-up treatments.

By rotating the ring nut 32 so that the zero value of the first graduated scale S1 or of the second graduated scale S2 is at the indicating element 35, the device 1 is in a non-operating condition, because the support element 13 is so positioned that the needles 14, 25 cannot exit the end 6 of the body 2, not even when the support element 13 is in said end position.

When on the other hand, the ring nut 32 is so rotated that at the indicating element 35 there is a value other than zero from the respective graduated scale, the device 1 according to the invention is in an operating position and is so adjusted that, when the support element 13 is in said end position, the needles 14, 25 protrude from the first end 6 of the body 2 by a quantity in tenths of millimetres, or in millimetres, equal in value to the respective graduated scale that is at the indicating element 35.

The possibility of using different adjusting scales depending on the type of needle-holding cartridge used and the fact that all types of cartridge can be fitted to the same body 2 confers maximum possible flexibility and precision to the device 1 according to the invention.

Figure 8:
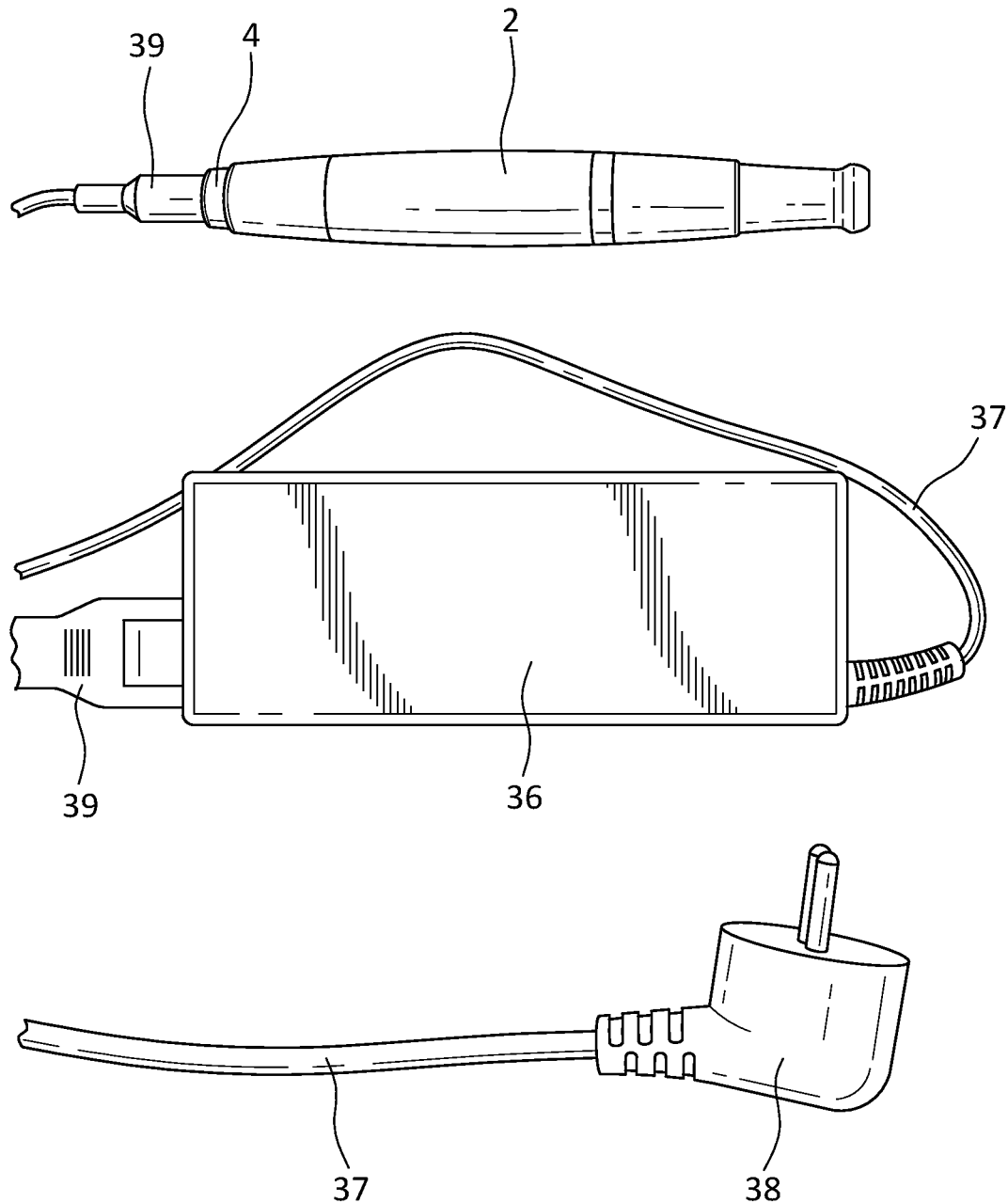
FIG. 8 illustrates the device according to the invention connected to a supply unit.

In FIG. 8, the device 1 according to the invention is illustrated connected to a feeder 36 by means of which the device 21 can be connected to an electric supply network.

The driver 36 is provided with a first cable 37, with a plug connecting element 38 by means of which the feeder 36 can be connected to a socket of an electric circuit. The feeder 36 is further provided with a second cable 39 that can be connected to the first end 4 of the body 2 to drive the drive motor of the device 1.

The drive motor of the device 1 can be supplied by a rechargeable battery (not visible in the figures) housed in the body 2, in which case the feeder 36 is used to recharge said battery.

The invention claimed is:

1. A device for cosmetic treatment comprising a body consisting of a first section, arranged at a first end of the body, in which a drive motor of the device is arranged, a second section, arranged at a second end of the body, opposite the first end, in which a needle-holding cartridge is fitted, and a third section, that connects the first section to the second section, in which a drive means is housed, wherein said needle-holding cartridge comprises a support element configured for supporting a single needle, or a plurality of needles, wherein said support element is movable inside a casing of said needle-holding cartridge and is driven to move inside said casing by said drive means between a start position in which said needle(s) do not protrude outside said body and an end position in which said needle(s) protrude from said body for a preset distance, wherein said third section comprises an adjusting ring nut rotatable around a longitudinal axis of the body, wherein a rotation of said adjusting ring nut determines a variation of the start position of said support element and of said preset distance, characterized in that on an outer surface of the adjusting ring nut a first graduated scale and a second graduated scale are impressed and on the second section of the body an indicating element is impressed that is associated with both the graduated scales, said first graduated scale and said second graduated scale indicating values of said preset distance.

2. The device of claim 1, wherein said first graduated scale comprises values between 0 and 0.3 mm and is associated with said needle-holding cartridge so configured that a maximum protrusion of the needle(s) from the body of the device, when the support element is in said end position, is not greater than 0.3 mm.

3. The device of claim 1, wherein said second graduated scale comprises values between 0 and 2.5 mm and is associated with said needle-holding cartridge so configured that a maximum protrusion of the needle(s) from the body of the device, when the support element is in said end position, is not greater than 2.5 mm.

4. The device of claim 1, wherein said casing is provided with a hole, or with a first opening, placed at a first end of the casing, said needle(s) protruding from said hole or from said first opening when said support element is in said end position, wherein said support element is provided with a rod-shaped appendage that protrudes from the casing through a second opening placed at a second end of the casing, opposite the first end, wherein said appendage interacts with said drive means.

5. The device of claim 4, wherein on said appendage a coil spring is fitted, arranged between a first collar that is part of the appendage and a second collar obtained in the casing.

6. The device of claim 1, wherein said casing is provided with an outer thread by which the needle-holding cartridge is configured to be tightened in a threaded hole made at the second end of the body.

7. The device of claim 4, wherein said drive means comprises a first disc-shaped thrust element, fitted inclined with respect to said longitudinal axis on an outlet shaft of the drive motor of the device, a further disc fitted to a first end of a rod-shaped second thrust element, arranged along said longitudinal axis, wherein said first thrust element interacts periodically with said further disc by exerting thereupon a thrust that is variable between a minimum value and a maximum value, and vice versa, wherein a second end of said second thrust element is in contact with the appendage of the support element when said needle-holding cartridge is screwed into a threaded hole.

8. The device of claim 1, wherein said drive motor is supplied by a feeder that is connectable to a power grid and to the drive motor.

9. The device of claim 1, wherein said drive motor is supplied by a rechargeable battery housed in the body.

* * * * *